US00PP12725P2

(12) United States Plant Patent
Fruehwirth

(10) Patent No.: US PP12,725 P2
(45) Date of Patent: Jun. 25, 2002

(54) POINSETTIA PLANT NAMED 'ECKADRIA'

(75) Inventor: Franz Fruehwirth, Encinitas, CA (US)

(73) Assignee: Paul Ecke Ranch, Encinitas, CA (US)

( * ) Notice: Subject to any disclaimer, the term of this patent is extended or adjusted under 35 U.S.C. 154(b) by 6 days.

(21) Appl. No.: 09/779,349

(22) Filed: Feb. 9, 2001

(51) Int. Cl.[7] ..... A01H 5/00
(52) U.S. Cl. ..... Plt./303
(58) Field of Search ..... Plt./303

*Primary Examiner*—Bruce R. Campell
*Assistant Examiner*—Annette H. Para
(74) *Attorney, Agent, or Firm*—C. A. Whealy

(57) ABSTRACT

A new and distinct cultivar of Poinsettia plant named 'Eckadria', characterized by its inflorescences with red and pink bi-colored flower bracts and large cyathia clusters; dark green-colored leaves with burgundy-colored petioles; upright and uniform plant habit; freely branching habit; early flowering, natural season flower maturity date is November 18 for plants grown in Encinitas, Calif.; response time, about 7.5 weeks; and excellent post-production longevity.

2 Drawing Sheets

BACKGROUND OF THE INVENTION

The present Invention relates to a new and distinct cultivar of Poinsettia plant, botanically known as *Euphorbia pulcherrima* Willd., and hereinafter referred to by the name 'Eckadria'.

The new Poinsettia a product of a planned breeding program conducted by the Inventor in Encinitas, Calif. The objective of the breeding program is to create new Poinsettia cultivars having flower bracts with desirable colors, uniform plant habit and excellent post-production longevity.

The new Poinsettia is a naturally-occurring whole plant mutation of the Poinsettia cultivar 490, disclosed in U.S. Plant Pat. No. 7,825. The new Poinsettia was discovered and selected by the Inventor as a single flowering plant within a population of plants of the parent cultivar in a controlled environment in Encinitas, Calif., in December, 1997. The selection of this plant was based on its attractive flower bract colors and good plant form and substance.

Asexual reproduction of the new Poinsettia by terminal cuttings taken at Encinitas, Calif., since 1998, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Eckadria'. These characteristics in combination distinguish 'Eckadria' as a new and distinct cultivar:

1. Inflorescences with red and pink bi-colored flower bracts and large cyathia clusters.
2. Dark green-colored leaves with burgundy-colored petioles.
3. Upright and uniform plant habit.
4. Freely branching habit.
5. Early flowering, natural season flower maturity date is November 18 for plants grown in Encinitas, Calif.; response time, about 7.5 weeks.
6. Excellent post-production longevity.

Plants of the new Poinsettia differ primarily from plants of the mutation parent, the cultivar 490, in flower bract color.

In addition, flower bracts of the new Poinsettia are orientated more upright than flower bracts of plants of the cultivar 490.

Plants of the new Poinsettia can be compared to plants of the Poinsettia cultivar 490 Jingle Bells, disclosed in U.S. Plant Pat. No. 8,771. In side-by-side comparisons conducted in Encinitas, Calif., plants of the new Poinsettia differed from plants of the cultivar 490 Jingle Bells in the following characteristics:

1. Plants of the new Poinsettia are taller and more upright than plants of the cultivar 490 Jingle Bells.
2. Plants of the new Poinsettia have narrower and more pointed flower bracts than plants of the cultivar 490 Jingle Bells.
3. Flower bracts of plants of the new Poinsettia have more pink coloration than flower bracts of plants of the cultivar 490 Jingle Bells.
4. Cyathia clusters of plants of the new Poinsettia are more open than cyathia clusters of the cultivar 490 Jingle Bells.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the colors of the new Poinsettia.

The photograph on the first sheet comprises a side perspective view of a typical plant of 'Eckadria'.

The photograph at the top of the second sheet comprises a top perspective view of a typical plant of 'Eckadria'.

The photograph at the bottom of the second sheet is a close-up view of typical leaves and flower bracts of 'Eckadria' (top) and '490 Jingle Bells' (bottom). Plants used in the photographs were about 16 weeks old.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements describe plants grown in Encinitas, Calif., under commercial practice in a glass-covered greenhouse with day temperatures about 24° C., night temperatures about 19° C., and light levels about 4,000 foot-candles. Single plants were grown in 16.5-cm pots, pinched one time, and flowered under naturally lengthening nyctoperiods during the fall. Plants used for the description were about 16 weeks old.

In the following description, color references are made to The Royal Horticultural Society Colour Chart except where general terms of ordinary dictionary significance are used.

Botanical classification: *Euphorbia pulcherrima* Willd. cultivar Eckadria.

Parentage: Naturally-occurring whole plant mutation of *Euphorbia pulcherrima* Willd. cultivar 490, disclosed in U.S. Plant Pat. No. 7,825.

Propagation:

*Type cutting.*—Terminal cuttings.

*Time to initiate roots.*—About 10 days at 20 to 22° C.

*Time to develop roots.*—About 28 days at 20 to 22° C.

*Rooting habit.*—Thick, fibrous and freely-branching.

Plant description:

*Plant form.*—Inverted triangle, top of plant rounded; mounding.

*Growth habit.*—Upright and uniform plant habit. Upright branch angle; thick, strong lateral branches. Freely branching; branching is enhanced by removing the shoot apex; about 7 lateral branches develop after removal of the terminal apex. Vigorous.

*Plant height.*—About 38 cm.

*Plant diameter or spread.*—About 61 cm.

*Crop time.*—From unrooted cuttings to a flowering plant in a 16.5-cm container, about 16 weeks are required.

*Stem description.*—Lateral branch length: About 28 cm. Lateral branch diameter: About 1.5 cm. Internode length: About 3.75 cm. Stem color: 146A.

*Foliage description.*—Alternate, simple. Quantity of leaves per lateral branch: About 10. Length: About 11 cm. Width: About 8 cm. Shape: Mostly ovate with irregular lobing. Apex. Acute. Base: Rounded to acute. Margin: Entire. Texture: Mostly glabrous with very slight pubescence on lower surface. Surface: Smooth, slightly rugose. Color: Young foliage, upper surface: Darker than 147A. Young foliage, lower surface: 137A. Mature foliage, upper surface: Darker than 147A; venation, 147C. Mature foliage, lower surface: 137A; venation, 147C to 147D. Petiole: Length: About 1 cm. Diameter: About 3 mm. Color: 60B.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long nyctoperiod conditions. Early flowering, response time, about 7.5 weeks; natural season flower maturity date is November 18 for plants grown in Encinitas, Calif.

*Post-production longevity.*—Plants of the new Poinsettia maintain good substance and bract color for about 4 to 6 weeks under interior conditions and for about 8 weeks under greenhouse conditions.

*Quantity of inflorescences.*—One per lateral branch, usually about 7 per plant.

*Inflorescence size.*—Diameter: About 30 cm. Height (depth): About 5.5 cm.

*Flower bracts.*—Quantity of flower bracts per inflorescence: Usually about 14 primary bracts and about 6 or 8 smaller secondary bracts per inflorescence. Length, largest bracts: About 15.5 cm; stalk about 1.2 cm. Width, largest bracts: About 8.5 cm. Shape: Mostly ovate with some irregular lobing on older bracts. Apex: Acute. Base: Acute. Margin: Entire. Texture: Glabrous, velvety. Surface: Smooth, slightly rugose. Orientation: Initially upright to horizontal to slightly recurved with development. Color: Developing, upper surface: Ground color, 53B, flecked with 52B. Developing, lower surface: Ground color, 53C, flecked with 52B to 52C. Mature, upper surface: Ground color, brighter than 53B, flecked with 54A, 54B and 54C; flower color does not fade with subsequent development. Mature, lower surface: Ground color, 53C, flecked with 54C to 54D.

*Cyathia.*—Quantity: Usually about 14 per corymb. Diameter of cyathia cluster: About 2 by 4 cm. Length: About 9 mm. Width: About 5 mm. Shape: Rounded ovate. Color: Immature: 144C. Mature: 144B. Peduncle: Length: About 4 mm. Aspect: Strong, erect. Color: 144B. Stamens: Stamen number: Typically at least 20 per cyathium. Anther shape: Oval. Anther length: About 1 mm. Anther color: 22B. Amount of pollen: Moderate. Pollen color: 16A. Pistils: Not observed. Nectary number: One per cyathia. Nectary color: 14B.

Disease resistance: Resistance to pathogens common to Poinsettias has not been observed on plants grown under commercial conditions.

It is claimed:

1. A new and distinct cultivar of Poinsettia plant named 'Eckadria', as illustrated and described.

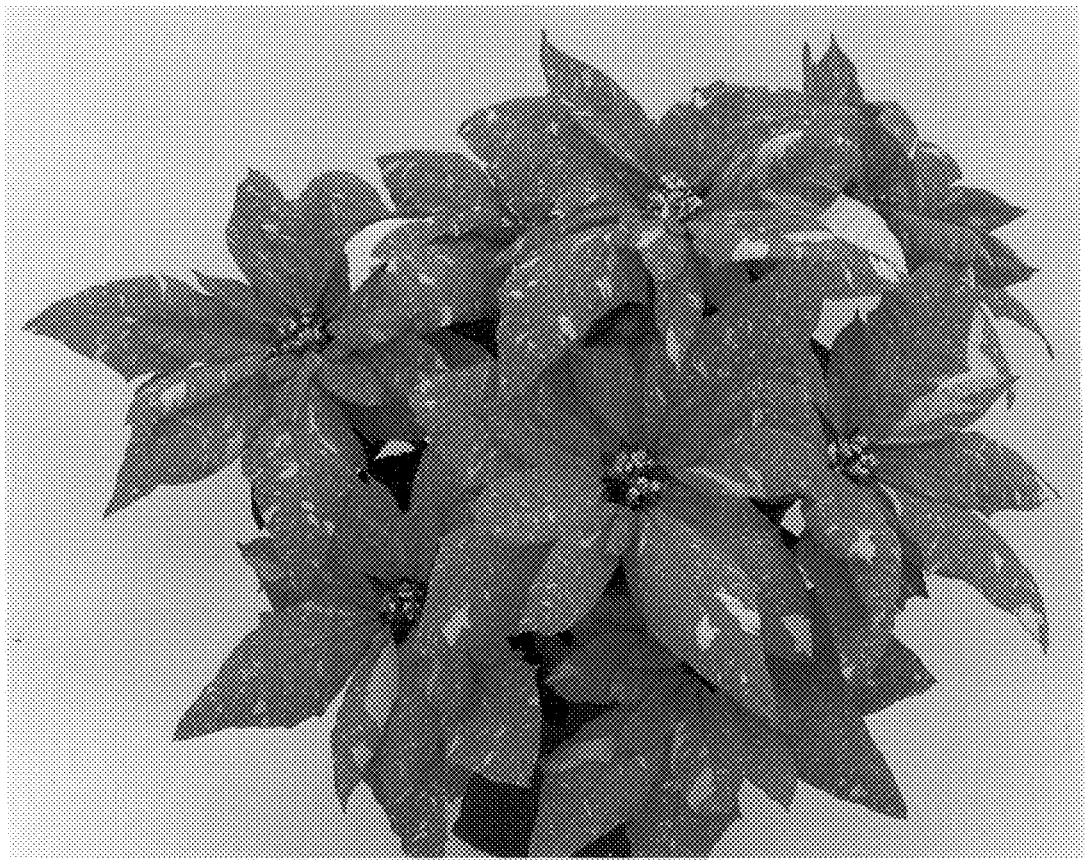

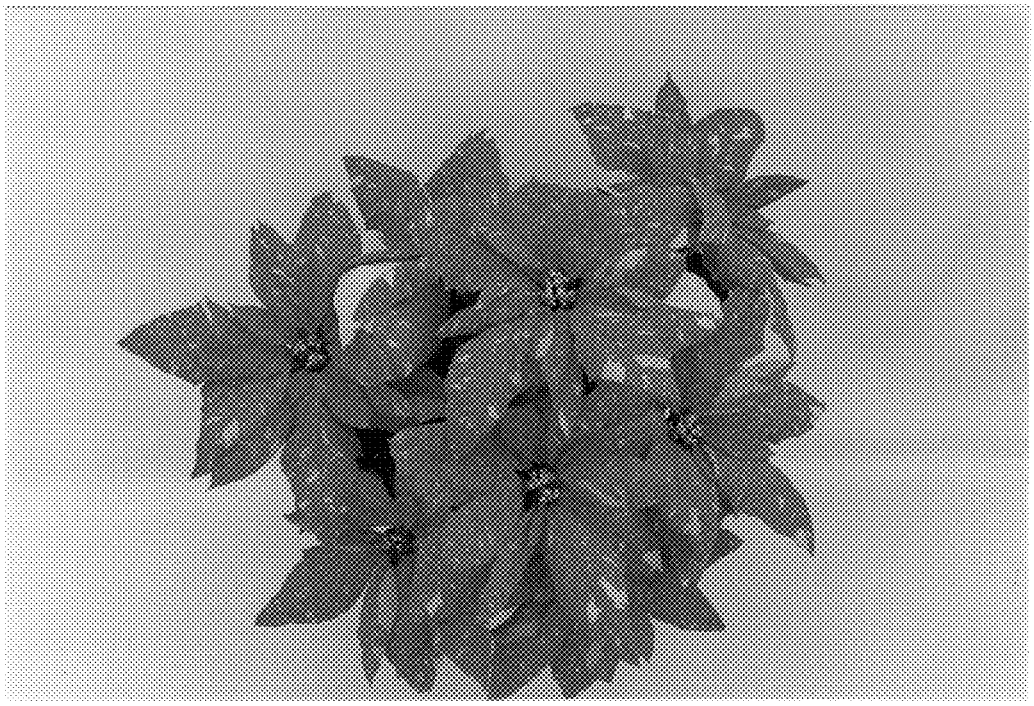
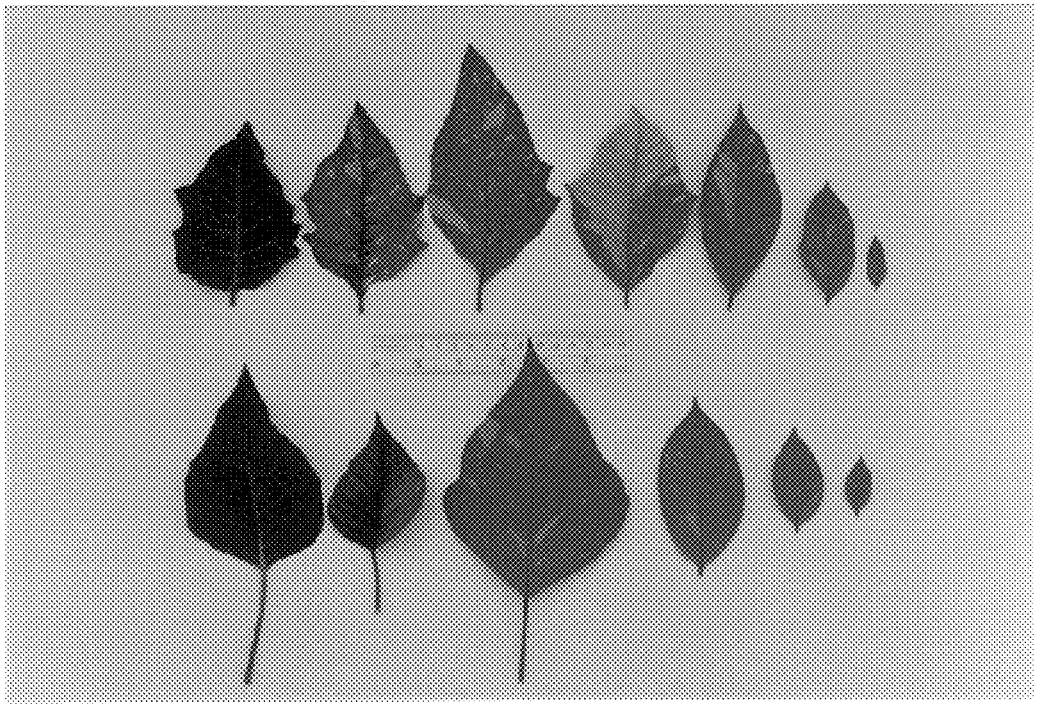

* * * * *